United States Patent [19]

Cote

[11] Patent Number: 5,597,527
[45] Date of Patent: Jan. 28, 1997

[54] THERMOMAGNETIC APPARATUS FOR DETERMINING OPTIMUM HEAT TREATMENT OF ALLOYS

[75] Inventor: Paul J. Cote, Clifton Park, N.Y.

[73] Assignee: The United States of America as represented by the Secretary of the Army, Washington, D.C.

[21] Appl. No.: 462,989

[22] Filed: Jun. 1, 1995

[51] Int. Cl.$^6$ .................................................. C21B 7/24
[52] U.S. Cl. ................................ 266/80; 266/90; 266/260
[58] Field of Search .................................. 148/508, 509; 266/80, 90, 78, 259, 260

[56] References Cited

U.S. PATENT DOCUMENTS

| | | | |
|---|---|---|---|
| 4,098,624 | 7/1978 | Laird, Jr. ........................... | 148/153 |
| 4,105,971 | 8/1978 | Nevalainen ......................... | 324/203 |
| 4,675,057 | 6/1987 | Pfaffmann et al. .................... | 148/509 |

OTHER PUBLICATIONS

Buhr et al, Transformation Products in Cold-Worked Austenitic Manganese Steel, Transactions, American Society For Metals, vol. 49.

Mentser, Magnetic Analysis of Phase Changes Produced in Tempering a High Carbon Steel, Transactions, American Society For Metals, vol. 51.

*Primary Examiner*—Scott Kastler
*Attorney, Agent, or Firm*—Edward Goldberg; Michael C. Sachs; John E. Callaghan

[57] ABSTRACT

The disclosure is of apparatus for determining the transformation characteristics of a metal alloy by treating the alloy to render it austenitic and then monitoring the isothermal decomposition of the austenite by measuring the magnetic change in the alloy.

2 Claims, 1 Drawing Sheet

THERMOMAGNETIC APPARATUS FOR DETERMINING OPTIMUM HEAT TREATMENT OF ALLOYS

The invention described herein may be manufactured, used and licensed by or for the Government for Governmental purposes without the payment of any royalties thereon.

BACKGROUND OF THE INVENTION

This invention relates to the determination of the optimum isothermal heat treatment procedure for alloys such as steel and austempered ductile iron. For years, workers have followed various procedures to determine the transformation characterstics and proper heat treatment procedures to obtain the optimum properties for a given alloy.

There are many problems associated with the various methods employed for these purposes in the past. The original method, which is still used, was a trial and error method. Another method presently used includes the steps of preparing a number of specimens, austenitizing them at appropriate temperatures and then cooling them rapidly by immersion in a liquid maintained at a lower temperature where the transformation of austenite into the desired microstructure (e.g. bainite, martensite) occurs. The specimens are then removed and examined to determine the microstructure.

An improved method uses metallurgical "quench" dilatometers which use a hollow specimen that can be quickly cooled from austenitizing temperatures under controlled conditions by a controlled combination of R.F. heating and gas cooling. The progress of the transformation in this type of system is monitored dilatometrically (i.e. by measuring length changes that accompany the phase transformation).

The metallurgical dilatometer is an excellent tool however it has the disadvantage of using relatively complex instrumentation with associated maintenance difficulties. In addition, false results are often obtained.

SUMMARY OF THE INVENTION

Briefly, the present invention utilizes magnetic properties of alloys and takes advantage of the dramatic difference in magnetic states of austenite, which is paramagnetic, and austenite decomposition products which are ferromagnetic. With the apparatus of the invention, a specimen is austenitized in a high temperature furnace and then it is rapidly cooled in a low temperature furnace where the austenite decomposition occurs. The change in phase within the specimen is monitored magnetically by means of coils which surround the low temperature furnace.

The present invention permits the monitoring of a transformation as it occurs and permits the same specimen to be used many times so that all of the main transformation characteristics can be obtained from a single specimen. In this way, the costly, time consuming specimen preparation processes of prior art methods are eliminated.

DESCRIPTION OF THE INVENTION

Figure 1:
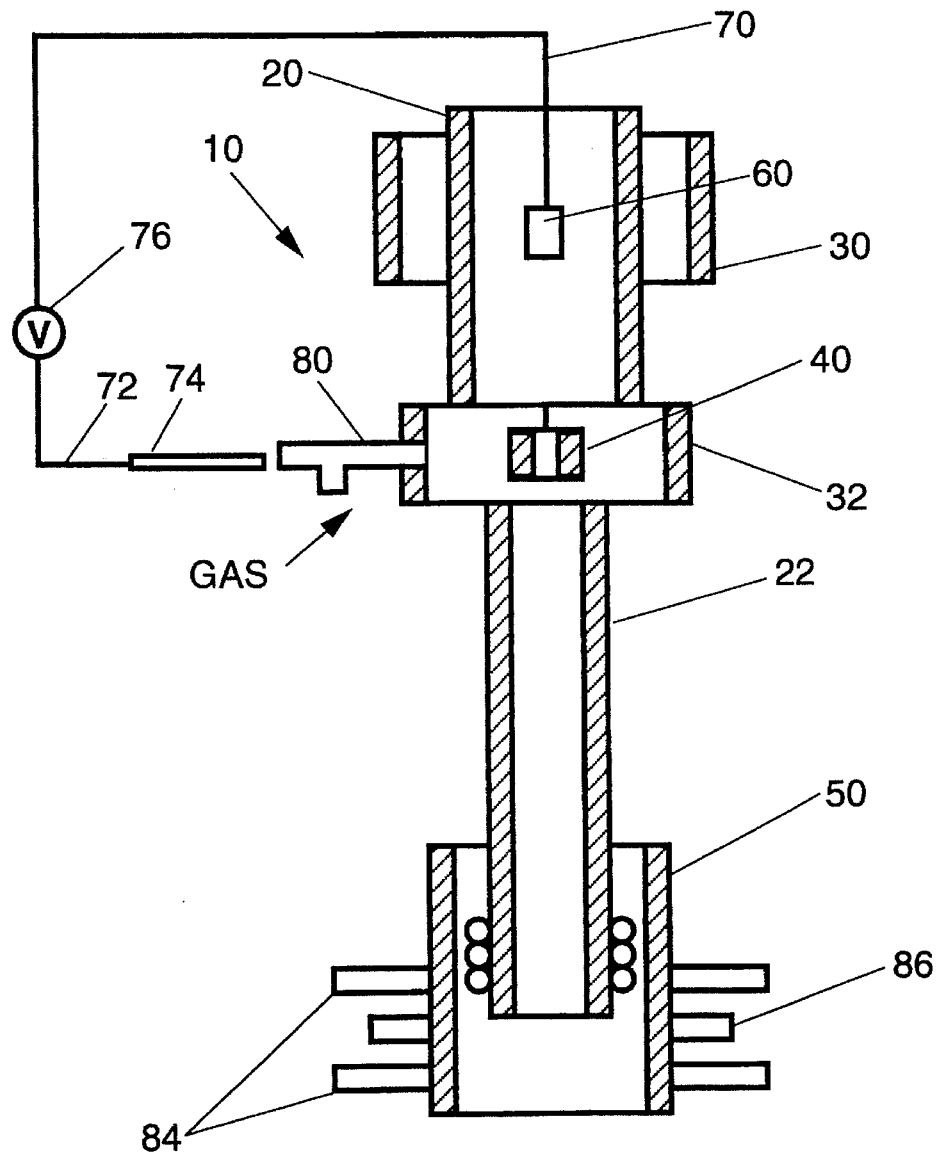
FIG. 1 is a schematic representation of apparatus embodying the invention.

The present invention has been utilized primarily with austempered ductile iron (ADI) however it has broad applicability to other alloys that are subjected to similar austenitizing and cooling transformation in their thermal processing.

Referring to the drawings, thermomagnetic processing apparatus 10 embodying the invention includes an upper quartz tube 20 oriented vertically with an austenitizing furnace 30 enclosing the tube adjacent its upper end. The furnace is a standard furnace which is capable of maintaining temperatures up to about 1200 degrees C.

The lower end of the quartz tube 20 is secured to a coupling 32, for example of brass, by threading or other suitable means. A lower metal tube of, for example stainless steel, 22 has its upper end threadedly coupled to the coupling 32 and it extends downwardly therefrom.

A quench block 40 is mounted within the coupling 32. The quench block is in the form of a hollow tubular block of metal or ceramic having an axial through hole 42 to allow a specimen to be inserted to be quenched. A hole 44 is drilled radially into the the quench block to join the axial hole 42 and to allow a thermocouple to be inserted. The quench block 40 is made of a metal or ceramic of sufficient mass to absorb heat from the specimen as required.

A lower furnace 50 used for isothermal transformations is disposed about the lower metal tube 22. This furnace, in one embodiment has a diameter of one inch and is vacuum jacketed and fabricated of non-magnetic materials and is capable of maintaining isothermal temperatures up to 600 degrees C.

A specimen 60 to be treated and analyzed is secured to a fine wire 70 by which the specimen can be raised and lowered within the quartz tube 20 and metal tube 22. According to the invention, the fine wire 70 forms one part of a thermocouple and has a diamter of about 0.005 inch to provide minimal friction and drag on the specimen as it is released from the quench block as described below. The wire is spot welded directly to the specimen to form one leg of a thermocouple. The other leg of the thermocouple is a sharpened 0.020 inch wire 72 which serves as the pinning assembly that is enclosed in a sheath of insulating material such as alumina, and inserted through the hole 44 in the side of the quench block and into the center of the block.

A purge gas inlet pipe 80 is also coupled into the quench block and is used for introducing a purge gas which is used to protect the specimen from oxidation at high temperatures. The sheathed wire 74 is introduced into the quench block through the pipe 80.

The specimen 60 is copper coated and the suspension wire 70 can be copper while the pinning wire 72 may be constantan thermocouple wire so that the system operates as a copper constantan thermocouple. Other thermocouple pairs such as chromel-alumel will also operate satisfactorily.

The wires 70 and 72 are connected to a voltmeter 76.

When the pinning wire 72 contacts the specimen, the thermocouple circuit is completed and the arrangement provides dynamic, accurate, instantaneous measurement of the specimen temperature.

The progress of the isothermal transformation from non-ferromagnetic austenite to the various ferromagnetic decomposition products, such as bainite, is monitored magnetically in the apparatus of the invention by means of a set of electrical coils that surround the specimen and lower furnace. The coil set includes a primary coil 84 which magnetizes the specimen with an alternating field and a secondary coil 86 which detects the extent of magnetization of the specimen. A pickup or sensing coil 88 is embedded in the driver coil 84 and thus is also mounted on the tube and it is coupled to display and computer instrumentation for data recording and control of operations.

The sensing coil output is analyzed in a standard manner to provide a digital output to a computer of the real and imaginary parts of the coil/specimen impedance. It is the imaginary component that is approximately linearly related to the volume of transformed austenite.

In one embodiment of the invention, a commercial coil system used was made by Forster instruments and is known as Magnatest-S. The driving coil provides sufficient magnetic driving force to magnetize a sample in the approximately linear range and provide a detectable response for the sensing coil which, as noted, is embedded within the driver coil.

The high sensitivity of the coil system permits measurements at low frequency, e.g. 16 Hz, which allows the signal to penetrate the entire volume of the ferromagnetic sample. The output of the pickup coil is registered digitally as real and imaginary components of the secondary coil impedance. The dominant contribution is the imaginary component from the coil impedance.

In the apparatus 10, the quartz tube 20 has a diameter of about one inch and the austempering furnace has a diameter of about 0.75 inch. The furnace is vacuum jacketed for maximum thermal isolation to avoid undue heating of the close fitting coil arrangement. The furnace windings are specially wound bifilarly to preclude spurious magnetic fields in the pickup coil. It is desirable that the magnetic response (coil/specimen impedance) be approximately proportional to the volume transformed and for this, it is important that the specimen be fabricated in rod form with a proper length to diameter ratio. One suitable specimen was ⅛ by ¾ inches.

Because the specimens are thin it is essential that their surfaces be protected from degradation by oxidation and decarburization at high temperatures. This is accomplished by electroplating the specimens with copper and providing a continuous flow of protective atmosphere such as 90 percent helium and 10 percent hydrogen during thermal treatment through pipe 80.

The method of the invention is as follows. First the alloy specimen to be analyzed is prepared in rod form with typical dimensions being approximately ⅛ inch diameter by ¾ inch length. The alloy may be, for example, ASTMA723 steel.

Next the specimen is electroplated with a thin layer of copper of a minimum of 0.002". The layer may also be thicker.

Next the specimen is attached to the fine wire 70 of for example 0.005 inch chromel thermocouple wire.

The specimen is lowered by way of the wire 70 into the quartz tube 20 and into the austenitizing furnace and maintained therein at temperature and for a desired time. The time in this furnace is not critical and may be about 15 minutes at about 850 degrees C.

Figure 2:
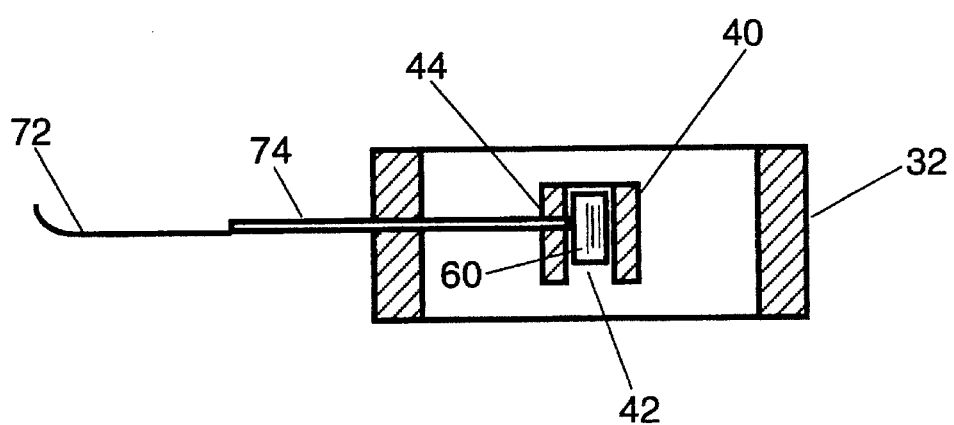
FIG. 2 is an enlarged sectional view of a portion of the apparatus shown in FIG. 1.

Next, the specimen is lowered into the quench block and pinned there by the wire 72 which is inserted through hole 44 into the axial opening in the quench block as shown in FIG. 2. The specimen is held in the quench block until the thermocouple voltage indicates that the desired target temperature has been reached. This time is usually about 10 seconds.

Next, pinning pressure by wire 72 is released and so that the specimen 60 is dropped into the low temperature furnace maintained at desired temperature and immediately begin monitoring magnetization output to register the progress of the transformation. Magnetization changes and time are recorded by a computer. Total times to completion typically range from one to 24 hours.

Finally, the data is analyzed to determine needed details of transformation for the specimen material. The apparatus is designed to measure the amount of material transformed as a function of time from non-magnetic austenite to ferromagnetic decomposition products such as bainite or pearlite at a given temperature. The increase in magnetic response as a function of time measures the amount transformed as a function of time. The specific measure used in this embodiment of the invention is the imaginary component of the complex impedance. These measurements are made over a range of temperatures. The resulting data represent the transformation characteristics of the alloy under study which can then be used by materials engineers to obtain the desired microstructure and material properties.

What is claimed is:

1. Apparatus for treating a metal alloy comprising a first insulating tube having an upper end and a lower end, a first high-temperature furnace at the upper end of said tube, means adjacent to said first tube for introducing a sample alloy, a quench block beneath the lower end of said first tube and aligned therewith, said quench block having an axial through-hole and a radial hole extending through its wall, a second tube extending beneath said first furnace, a coupling coupled between said first tube and said second tube, said quench block being disposed within said coupling, said coupling having a hole aligned with said axial hole in said quench block, a hollow pipe secured to said coupling and aligned with waid radial hole in said quench block, a thermocouple including a first wire secured to a specimen at the upper end of said first tube and a second wire insertable into said hollow pipe and into said quench block to contact a specimen therein, said first and second wires being coupled to measuring means, a second low-temperature furnace, electrical coils for generating an electric field enclosing said second tube near the lower end thereof and enclosing said low temperature furnace, and a pickup electrical coil enclosing said tube near the lower end thereof.

2. Apparatus for treating a metal alloy specimen comprising:

a first high temperature furnace for treating an alloy sample and rendering it austenitic;

a second low temperature furnace spaced from said first furnace;

quenching means disposed between said first furnace and said second furnace for rapidly reducing the temperature of a specimen heated in said first furnace, said quenching means comprising a hollow tube having an opening which extends from its outer wall into the interior thereof, and wherein said quenching means receives a sample held by a fine wire and a second wire is adapted to be inserted through said opening in said wall thereof to engage and hold said sample in place; and magnetic means associated with said second furnace for measuring the transformation character of a sample.

* * * * *